United States Patent
Sakuma et al.

(10) Patent No.: US 11,642,402 B2
(45) Date of Patent: May 9, 2023

(54) METHOD OF PRODUCING IMMUNOTHERAPY VACCINE

(71) Applicants: CyTIX Inc., Tokyo (JP); Kinko Capital Co., Ltd., Tokyo (JP)

(72) Inventors: Sadatoshi Sakuma, Tokyo (JP); Michiyo Osono, Tokyo (JP); Eriko Oka, Tokyo (JP)

(73) Assignees: CYTIX INC., Tokyo (JP); KINKO CAPITAL CO.. LTD., Tokyo (JP)

( * ) Notice: Subject to any disclaimer, the term of this patent is extended or adjusted under 35 U.S.C. 154(b) by 352 days.

(21) Appl. No.: 17/011,542

(22) Filed: Sep. 3, 2020

(65) Prior Publication Data
US 2021/0069311 A1 Mar. 11, 2021

(30) Foreign Application Priority Data
Sep. 9, 2019 (JP) .............................. JP2019-163625

(51) Int. Cl.
*A61K 39/00* (2006.01)
*C12N 5/0784* (2010.01)
*C12N 13/00* (2006.01)

(52) U.S. Cl.
CPC ........ *A61K 39/0011* (2013.01); *C12N 5/0639* (2013.01); *C12N 13/00* (2013.01); *A61K 2039/5154* (2013.01); *C12N 2502/1114* (2013.01)

(58) Field of Classification Search
CPC ........ A61K 39/0011; A61K 2039/5154; A61K 2039/5158; C12N 5/0639; C12N 13/00; C12N 2502/1114; C12N 2502/1121; C12N 2523/00; C12N 5/0693; A61P 35/00
See application file for complete search history.

(56) References Cited

FOREIGN PATENT DOCUMENTS

JP 2013-523824 A 6/2013

OTHER PUBLICATIONS

Chen, et al., Eur. J. Immunol. 2006 36:1598-1607 (Year: 2006).*
Brentz, et al., The Journal of Biological Chemistry 2013 288:36691-36702 (Year: 2013).*
Matsumoto et al., Possibility of developing next generation cancer vaccine therapy using secretory cell bodies (Exosomes), Japan Surgical Society Magazine, 2005, vol. 106, extra edition, p. 195, Abstract No. SF2309-2, Japan.
Koga et al., Application of cancer cell-derived Exosomes for the treatment of breast cancer, Biotherapy, 2004, vol. 18, Suppl. 1, p. 116, Abstract No. p. 27, Japan.
Dendritic cells pulsed with leukemia cell-derived Exosomes more efficiently include antileukemic immunities, PLOS ONE, 2004, vol. 9, No. 3, e91463, pp. 1-7, Japan.

* cited by examiner

*Primary Examiner* — Julie Wu
*Assistant Examiner* — John L Van Druff
(74) *Attorney, Agent, or Firm* — United IP Counselors, LLC

(57) ABSTRACT

A method of producing an immunotherapy vaccine is provided. The method includes performing a heat treatment to exosomes separated from cancer cells or body fluids including blood of a cancer patient to promote inactivation of proteolytic enzymes in the exosomes, and introducing or co-culturing the exosomes in dendritic cells derived from blood of the cancer patient or a healthy person to make antigen-presenting cells.

3 Claims, 5 Drawing Sheets
(4 of 5 Drawing Sheet(s) Filed in Color)

METHOD OF PRODUCING IMMUNOTHERAPY VACCINE

CROSS-REFERENCE TO RELATED APPLICATIONS

This application claims priority to Japanese Patent Application No. 2019-163625 filed on Sep. 9, 2019, which claims priority to Japanese Patent Application No. 2018-219559 filed on Nov. 22, 2018, and issued on Jan. 29, 2020 as Japanese Patent No. 6635637. The contents of those applications are incorporated by reference herein in their entireties.

TECHNICAL FIELD

The present invention relates to a method of producing a dendritic cell vaccine used in immunotherapy using exosomes of cancer cells and dendritic cells.

BACKGROUND ART

In immunotherapy, there are a therapy of presenting a specific antibody using a specific protein produced by cancer cells as an index to create immune cells (cytotoxic T cells (CTLs)) that attack the cancer cells (acquired immunity), and a therapy of recognizing foreign proteins to eliminate foreign substances (natural immunity). In conventional immunotherapy, dendritic cells (DCs) isolated from blood monocytes of a patient are fused with cancer cells (including precancerous cells) obtained from the patient, and then these fused cells are administered alone or with cytokines that stimulate a cytotoxic T cell response or a humoral immune response by subcutaneous injection or the like.

In this conventional immunotherapy, since the fusion efficiency of DCs and cancer cells is as low as around 10%, the antigen presentation efficiency of the administered vaccine is poor. On the other hand, when exosomes are introduced to DCs, $10^8$ to $10^9$ exosomes can be obtained with respect to $10^5$ DCs, and so exosomes are introduced into most DCs.

In addition, normal mature DC-derived exosomes and NK cell-derived exosomes cause inhibition of cancer cell proliferation, inhibition of regulatory T cells (Treg), inhibition of MDSC, and inhibition of angiogenesis, and also work to destroy cancer tissue. Therefore, mature DC-derived exosomes and natural killer (NK) cell-derived exosomes are in the process of being used for cancer treatment.

On the other hand, exosomes derived from cancer cells tend to allow cancer cells to worsen and mutate the genes thereof. In addition, the exosomes inhibit the activity of immune cells preventing cancer cell growth. In this case, the cancer cells escape from the antigen-presenting function of the DCs that make up of the vaccine, the fused cells act as antigen-presenting cells (APCs), and even if cytotoxic T cells (CTLs) and NK cells are induced, CU activity and NK activity are lost, which results in a loss of anticancer activity. That is, since the cancer cells escape from immunotherapy, exosomes derived from the cancer cells are released, with the genes thereof undergoing frequent mutation and the activity of immune cells being lost. No effective countermeasures against this situation have been established.

Japanese Unexamined Patent Application Publication (Translation of PCT Application) No. 2013-523824 has been proposed as prior art to solve the conventional problem of low fusion efficiency of DCs and cancer cells. In this document, exosomes released from cancer cells are inserted into immune cells such as DCs and T cells by electroporation, and the electroporated cells (vaccine) are then administered to a patient.

According to Japanese Unexamined Patent Application Publication (Translation of PCT Application) No. 2013-523824, the genes of cancer cells are constantly changing, and when the cancer cells mutate the genes thereof, proteins displayed by the cancer cells also change and escape from antigen presentation. Cell-derived exosomes maintain the equal proteins and functions as the cells that are the source of secretion. Exosomes released from cancer cells, not normal exosomes derived from DCs or NK cells, also have the equal proteins, that is, antigens, as the cancer cells that are the source of secretion. In other words, when cancer cell-derived exosomes are used, even if the cancer cell mutates the genes thereof, the mutated cancer cell-derived exosome has an antigen equivalent to that of the mutated cancer cell. Consequently, if exosomes derived from cancer cells are used as an antigen, even if the cancer cell genes change and the protein to be displayed is altered, the cancer cells cannot escape from antigen presentation because the protein is equal to the protein possessed by the exosomes derived from the cancer cells.

Further, Japan Surgical Society Magazine, 2005, vol. 106, extra edition, p. 195, Abstract No. SF2309-2 and Biotherapy, 2004, vol. 18, Suppl. 1, p. 116, Abstract No. p-27 disclose that by pulse-guiding exosomes derived from cancer cells to DCs, the DCs induced autologous tumor cytotoxic activity in the T cells of patients.

Moreover, PLOS ONE, 2004, vol. 9, no. 3, e91463, pp. 1-7 discloses that DCs stimulated with exosomes derived from leukemia cells induce a CU immune response against leukemia cells.

BRIEF SUMMARY

If exosomes released from cancer cells are fused with dendritic cells (DCs), and the fused cells are then administered to a patient as a vaccine, the vaccine will not lose the APC function even if the cancer cell genes mutate. Therefore, the methods disclosed in the prior art documents are effective.

It has turned out that the mechanism of antigen presentation includes decomposing a protein specific to a cancer cell into a peptide inside the cell, binding this peptide to an MHC molecule on the surface of the cancer cell to be presented as an antigen peptide, and recognizing this antigenic peptide by CTLs to attack the cancer cells.

However, it requires time for the proteins in exosomes to be decomposed into peptides, which hinders immune reactions. In other words, there is a problem of time required to exhibit the effect as a vaccine even if exosomes released from cancer cells are fused with DCs.

Also, there is a problem that exosomes cannot be stored for a long period of time. Exosomes to fuse with the DCs are required to be particles which maintain the membrane structure. However, since this membrane structure collapses after a certain period of time at room temperature, storage is not possible.

While long-term storage is possible at extremely low temperatures, such as −96° C., via cryopreservation, thawing must be carried out for vaccine production. Repeated thawing breaks down the membrane, which may result in the structure no longer being maintainable as particles. Storage at a low temperature of about 4° C. instead of cryopreservation is also conceivable. However, similar to particles of viruses (influenza, parainfluenza, herpes virus) having a membrane structure, inactivation (99%) occurs in about one month, the particles are destroyed, and the antigen-presenting efficiency deteriorates. Proteins can no longer be produced.

As cancer cells worsen, exosomes can carry the same antigens as their mother cells, and so possess an effective antigen presentation to mutation. The method of producing an immunotherapy vaccine for cancer according to the present invention includes separating exosomes from a culture fluid of cancer cells (including cancer stem cells) or body fluid such as blood or ascites of a cancer patient, inactivating the separated exosomes by heat treatment, and then introducing the inactivated exosomes to dendritic cells to be fused.

As described above, when left at room temperature for a certain period of time, the membrane structure of exosomes breaks down, which prevents fusion with DCs. Therefore, it is necessary to perform the heat treatment under the condition of maintaining the membrane structure of the exosomes while promoting the conversion of proteins into peptides, and this condition is 56° C. or less and 30 minutes or less. At higher temperature conditions, the protein is denatured, and the antigenicity thereof cannot be maintained.

The method of producing a vaccine used for cancer immunotherapy according to the present invention can use electroporation, PEG (polyethylene glycol), and the Sendai virus for introducing the exosomes separated from cancer cells or body fluids of patients to DCs.

In a case where electroporation is used, the exosomes are taken up instantaneously, and since $10^9$ or more exosome particles are present in 1 ml of the serum of a terminal cancer patient, the uptake rate to dendritic cells is believed to be 90% or more. Therefore, it is considered that the number of APCs is significantly increased as compared with the conventional fusion of DCs cells and cancer cells.

Also, exosomes can be separated from not only the blood of cancer patients but also body fluids such as urine and ascites.

According to the present invention, the antigen-presenting function is enhanced. As described above, cancer cell-specific proteins (proteins within exosomes) are decomposed into peptides, which bind to MHC molecules to be presented to cytotoxic T cells (CTLs) as antigen peptides. To maintain physiological activity, proteins have a three-dimensional structure so as not to be targeted by proteolytic enzymes and lipolytic enzymes such as protease and lipase. However, although the three-dimensional structure of the protein is not destroyed by the heat treatment of the present invention, mutation occurs only in the active group and so the enzyme activity is lost. Moreover, the cancer cell-specific protein is easily decomposed into peptides and binds to MHC molecules. Therefore, the antigen-presenting function for CTLs is enhanced.

As a secondary effect, proteolytic enzymes and lipolytic enzymes lose activity, the stability as exosome particles can be maintained, and long-term storage becomes possible. Further, heating the exosomes may increase the heat shock protein (HSP) expression. These HSPs are considered to have a function of enhancing immunity.

The HSPs are heat-resistant proteins that activate the entire immunity, and are activated rather than inactivated by heat treatment. For this reason, it is effective to use the heat-treated exosomes as an antigen.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

A preferred embodiment of the present invention will be described below. The scope of rights of the present invention is not limited by this embodiment.

(A) Extraction of Exosomes from Cell Culture Supernatant

Step 1: After culturing for 2 days in a medium supplemented with exosome-depleted fetal calf serum (FCS), exosomes were extracted from the culture supernatant. For the extraction, the miRCURY Exosome Cell/Urine/CSF Kit (Takara Bio Cat. 300102) is used as an isolation kit.

Step 2: The number of exosome particles extracted in Step 1 was counted.

Step 3: The exosomes were inactivated by performing a heat treatment (56° C. for 30 minutes).

The cell membrane of an exosome easily breaks down when heated. Fusion with DCs is not possible when the cell membrane has collapsed. From this viewpoint, the upper temperature limit and the upper time limit of the heat treatment were determined by changing the heating conditions. The determination was made by observing the membrane structure of the exosomes from microphotographs taken at each condition.

Figure 1:
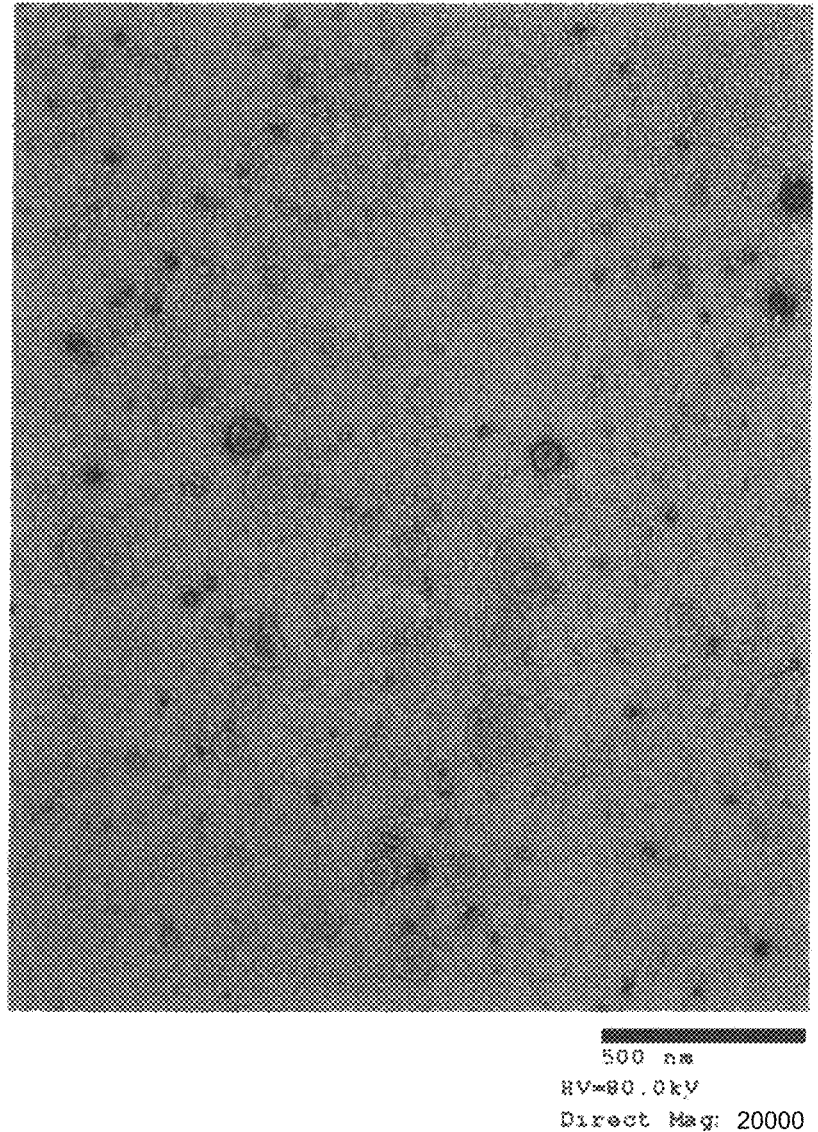
FIG. 1 is a microphotograph of exosomes with the heating conditions of 56° C. and 30 minutes.
Figure 2:
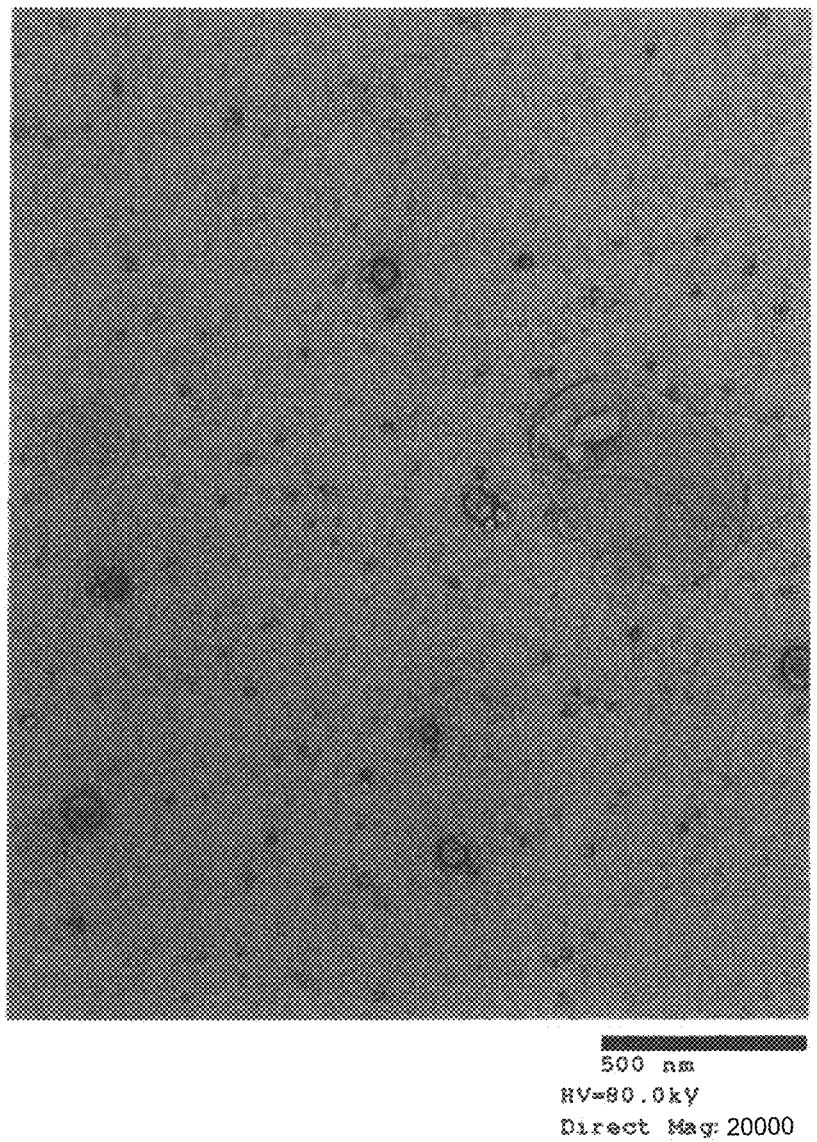
FIG. 2 is a microphotograph of exosomes with the heating conditions of 56° C. and 30 minutes.
Figure 3:
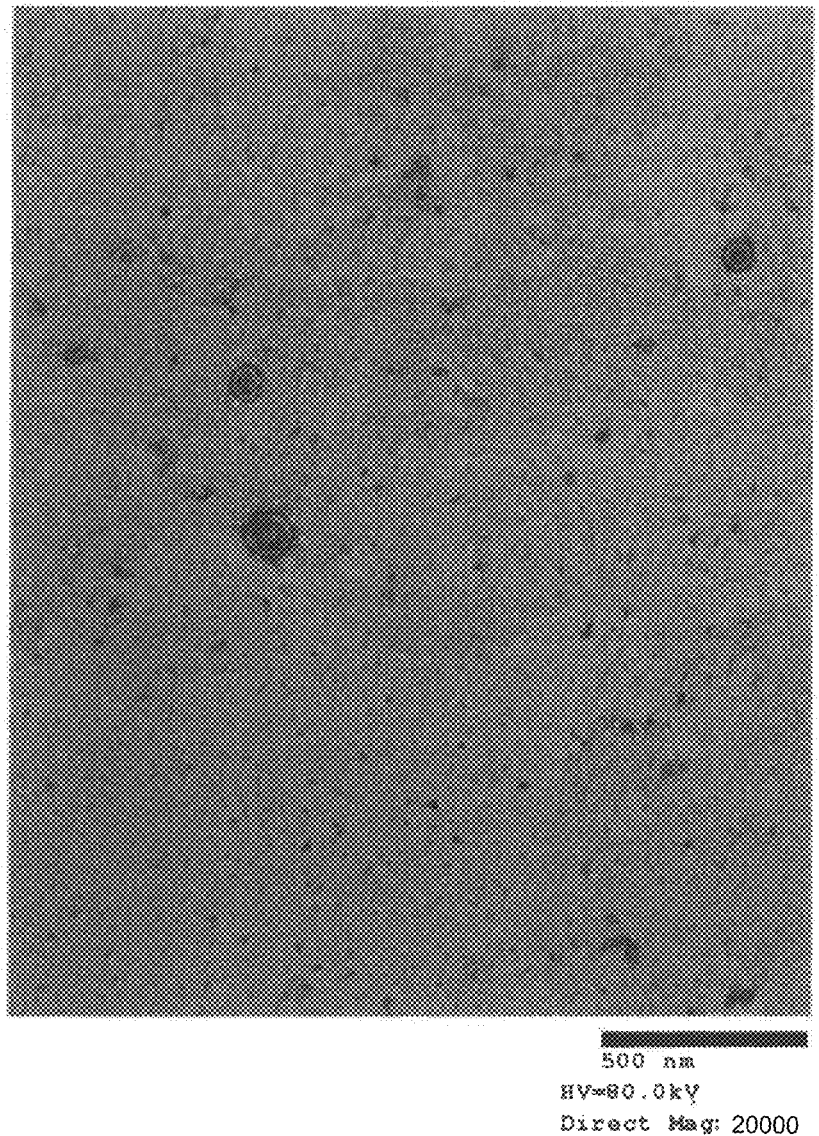
FIG. 3 is a microphotograph of exosomes with the heating conditions of 56° C. and 30 minutes.

In all of FIGS. 1 to 3, heating conditions of 56° C. for 30 minutes were selected. In each figure, the circular dark part shows the membrane structures maintained by exosomes, and the circular whitish part which is larger than the dark part shows exosomes in which the membrane structure has collapsed. No nucleus is found in exosomes where the membrane structure is maintained, providing confirmation that the exosome is secreted from the cytoplasm. Among exosomes whose membrane structure has collapsed, there are also those in which the nucleus has disappeared.

A temperature condition of less than 56° C., including 37° C. (body temperature), cannot be considered as heating, and so would be a normal exosome without denaturation of the active group of the enzyme. When the temperature exceeds 56° C., the number of exosomes whose membrane structure collapsed increased. The same applies to the treatment time. In the case of 56° C. for 30 minutes, as is clear from the microphotographs, exosomes in which the membrane structure has collapsed to some extent are also mixed therein. This proves that there are exosomes whose membrane structure has not collapsed and that the enzymatic denaturation in the exosomes is in progress. Therefore, it is desirable to perform the heat treatment under the conditions of 56° C. or lower and 30 minutes or less, and preferably close to 56° C. and 30 minutes as much as possible.

(B) Lysis of tumor cells by activated cytotoxic T cells (CTLs)

Step 1: After collecting blood from a healthy person, DCs were induced from peripheral blood mononuclear cells. Specifically, peripheral blood (50 ml) is collected. Then, centrifugation (c.f.g. 1800×g for 15 mins) is performed and the cells in the intermediate layer are collected. After this, the cells are washed twice with PBS (c.f.g. 1200 rpm for 5 mins), the number of cells is counted, and the cells are resuspended in a medium (CTS AIM V medium (Gibco, Thermo Fisher Scientific)) at $2 \times 10^6$/ml.

The cells are seeded at 1 ml/well in a 24-well plate and incubated at 37° C. in a 5% $CO_2$ incubator for 2 hours. Then, the floating cells are removed, and a medium for the DCs (AIM V medium supplemented with cytokines (final 10 ng/ml GM-CSF and IL-4, Miltenyi Biotec) and 2% autologous plasma) is added at 1 ml/well, whereupon culturing is commenced.

Subsequently, 500 ul of fresh dendritic cell medium is added to the well, and cytokines for maturation (final 10 ng/ml TNFα, Miltenyi Biotec) are added.

Step 2: The following test sections (1) to (3) were performed as antigen stimulation of DCs.
(1) Cellular fusion of DCs and tumor cells with PEG (polyethylene glycol)
(2) Electroporation of DCs and exosomes
(3) Co-culture of DCs and exosomes Step 3: Co-culture of DCs activated in the above test sections (1) to (3) and CTLs was performed.

Step 4: Co-culture of the above co-cultured CTLs and tumor cells was performed.

The lysis of the cytotoxic T cells (CTLs) was observed with an MTT assay. The results are shown in FIGS. 4 and 5.

Figure 4:
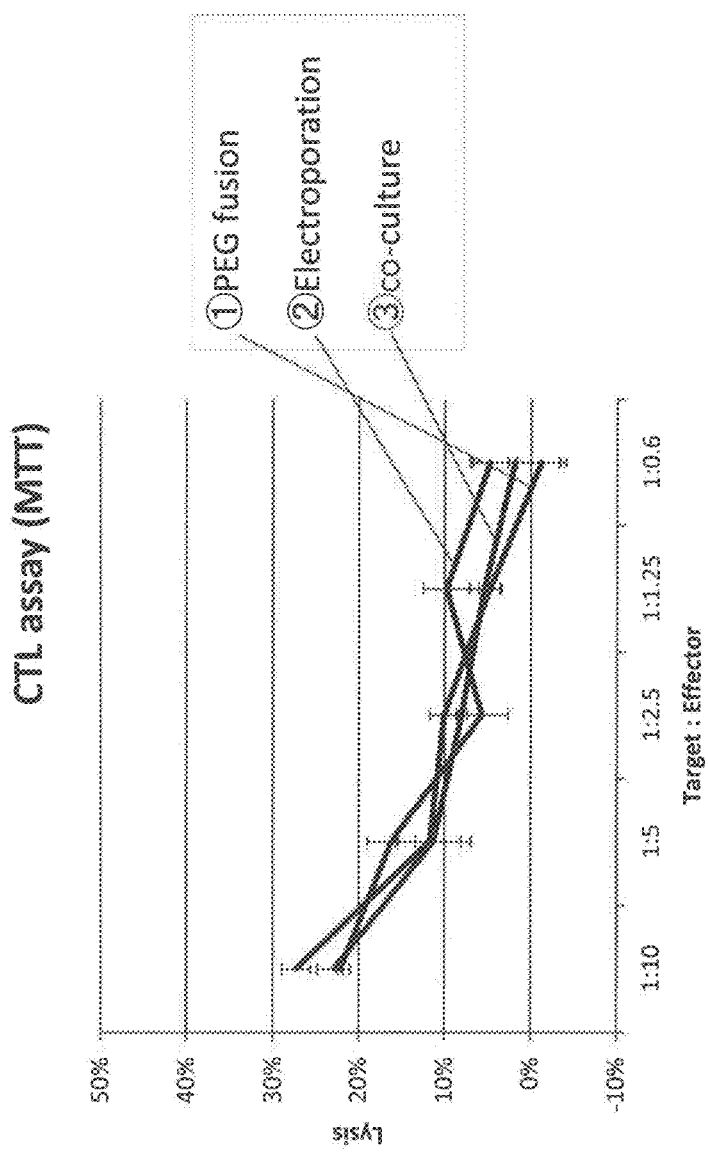
FIG. 4 is a graph showing the results of comparing the period after the heat treatment of heat-treated exosomes with the lysis activity (% of lysis).

FIG. 4 shows the relationship between the target:effector ratio and the lysis of CTLs. The CTLs in which exosomes heat-treated by the method of the present invention are introduced to DCs by electroporation to make antigens exhibit the equal lysis to CTLs obtained by cellular fusion with current PEG (polyethylene glycol) and co-culture.

In particular, when the effector is increased in the target:effector (horizontal axis), the lysis is higher than that of PEG cell fusion and co-culture.

Figure 5:
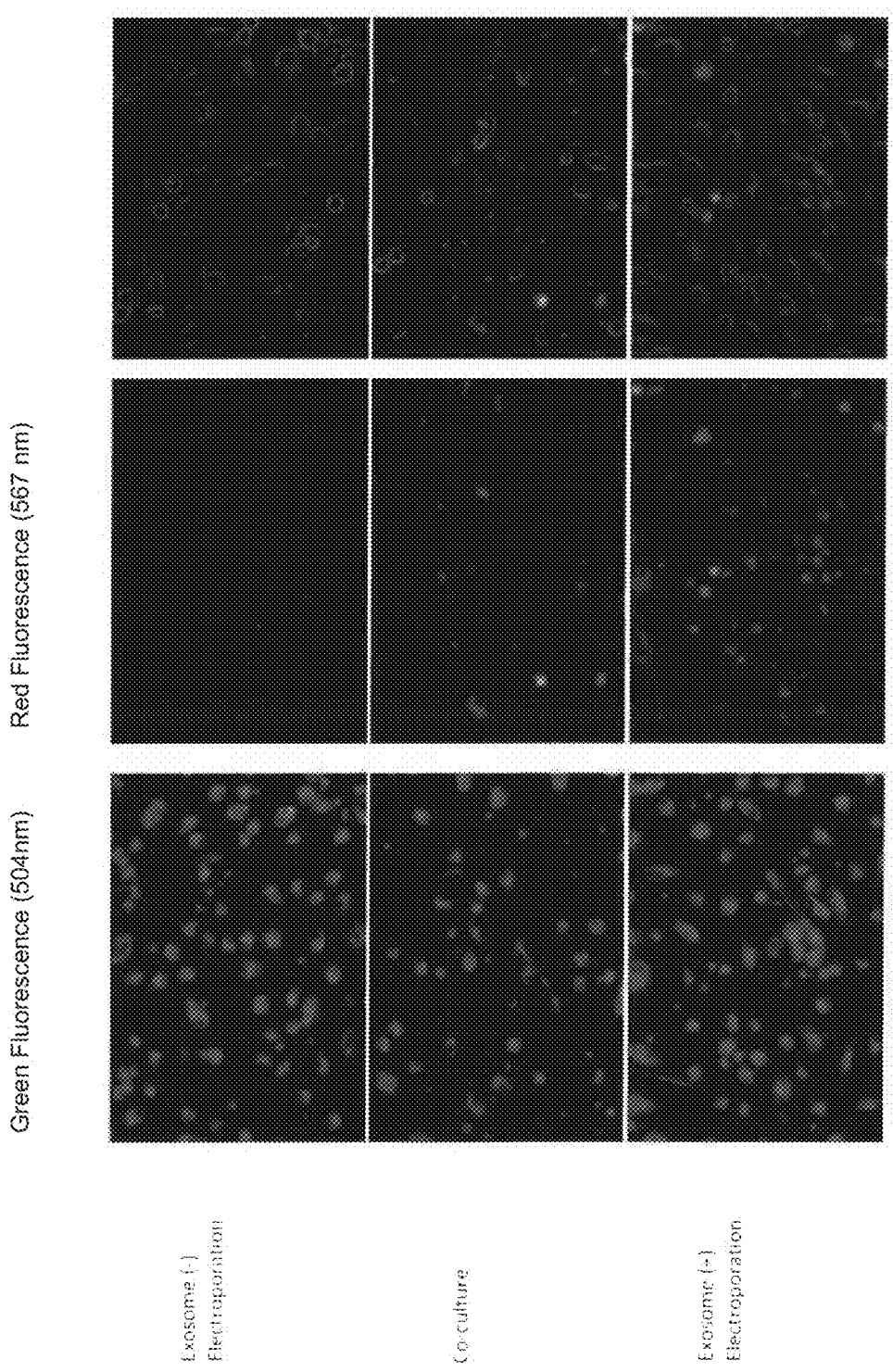
FIG. 5 is fluorescence (green fluorescence and red fluorescence) and bright-field microphotographs of proteins of dendritic cells (DCs) to which exosomes have been introduced, in which the upper row shows DCs to which non-heat treated exosomes have been introduced by electroporation, the middle row shows DCs to which exosomes heat-treated under the conditions of the present invention have been introduced by co-culturing, and the lower row shows DCs to which exosomes heat-treated under the conditions of the present invention have been introduced by electroporation.

Further, it can be seen from FIG. 5 that the expression amount of protein by exosomes when heat-treated increases. Therefore, the vaccine obtained by the method of the present invention is effective for immunotherapy.

The vaccine of the present invention, that is, a vaccine obtained by introducing heat-treated exosomes to DCs by electroporation or the like, functions as APCs. When these APCs are administered to the patient's body by subcutaneous injection or the like, the APCs migrate to the lymph node, educate the T cells in the lymph node, and thereby change the T cells to CTLs. As mentioned above, since the number of exosomes is extremely large compared to DCs, the number of DCs that take in exosomes is also large. As the number of such DCs increases, the number of APCs increases, and CTLs also increases, which enhances the immune effect.

It is also possible to co-culture DCs to which exosomes have been introduced with T cells so as to make CTLs that can be used as a vaccine.

What is claimed is:

1. A method of producing an immunotherapy vaccine, the method comprising:
   performing a heat treatment under a condition of 56° C. for 30 minutes on exosomes separated from cancer cells or bodily fluids from a cancer patient to promote inactivation of proteolytic enzymes in the exosomes; and
   introducing or co-culturing the exosomes in the presence of dendritic cells derived from blood from the cancer patient or a healthy person to make antigen-presenting cells.

2. The method of producing an immunotherapy vaccine according to claim 1, wherein the exosomes are maintained as stable particles by inactivating the proteolytic enzymes by the heat treatment.

3. The method of producing an immunotherapy vaccine according to claim 1, wherein the dendritic cells are co-cultured with T cells to make cytotoxic T cells.

* * * * *